(12) United States Patent
Busam et al.

(10) Patent No.: US 7,858,157 B2
(45) Date of Patent: Dec. 28, 2010

(54) ABSORBENT ARTICLES COMPRISING HYDROPHILIC NONWOVEN FABRICS

(75) Inventors: Ludwig Busam, Hunstetten (DE); Andreas Flohr, Kronberg (DE); Christofer Fuchs, Eschborn (DE); Ekaterina Anatolyevna Ponomarenko, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/402,561

(22) Filed: Mar. 12, 2009

(65) Prior Publication Data

US 2009/0176908 A1 Jul. 9, 2009

Related U.S. Application Data

(62) Division of application No. 10/674,670, filed on Sep. 30, 2003, now Pat. No. 7,521,587.

(30) Foreign Application Priority Data

Sep. 30, 2002 (EP) ................... 02021943

(51) Int. Cl.
*B05D 3/06* (2006.01)
(52) U.S. Cl. ................ 427/558; 604/367; 604/368; 442/170; 442/171
(58) Field of Classification Search ............. 604/367, 604/368; 427/558; 442/170, 171
See application file for complete search history.

(56) References Cited

U.S. PATENT DOCUMENTS 3,083,118 A * 3/1963 Bridgeford ................ 428/375
3,860,003 A 1/1975 Buell
4,834,735 A 5/1989 Alemany et al.
4,968,532 A 11/1990 Janssen et al.
5,037,416 A 8/1991 Allen et al.
5,269,775 A 12/1993 Freeland et al.
5,274,028 A 12/1993 Bertrand et al.
5,464,687 A * 11/1995 Sheth ....................... 442/361
5,569,234 A 10/1996 Buell et al.
5,625,222 A 4/1997 Yoneda et al.
5,830,604 A 11/1998 Singleton et al.
5,922,417 A * 7/1999 Singleton et al. ........... 427/558
6,004,306 A 12/1999 Robles et al.
6,118,218 A 9/2000 Yializis et al.
2005/0159720 A1 7/2005 Gentilcore et al.

FOREIGN PATENT DOCUMENTS

| EP | 1 164 157 A1 | 12/2001 |
|---|---|---|
| JP | 01-239101 | 3/1988 |
| JP | 63-063459 A | 3/1988 |
| JP | 01-292103 A | 11/1989 |
| WO | WO 93/01622 A1 | 1/1993 |
| WO | WO 93/04113 A1 | 3/1993 |
| WO | WO 95/25495 A1 | 9/1995 |
| WO | WO 98/56326 A1 | 12/1998 |
| WO | WO 98/58108 A1 | 12/1998 |
| WO | WO 00/16913 A1 | 3/2000 |
| WO | WO 00/16914 A1 | 3/2000 |

* cited by examiner

*Primary Examiner*—Melanie J Hand
(74) *Attorney, Agent, or Firm*—John G. Powell; Kathleen Y. Carter

(57) ABSTRACT

A process for treating fibers to render the fibers more hydrophilic. The process includes contacting the fibers with a solution of hydrophilic monomers and radical polymerization initiators and exposing the fibers to UV radiation.

9 Claims, 2 Drawing Sheets

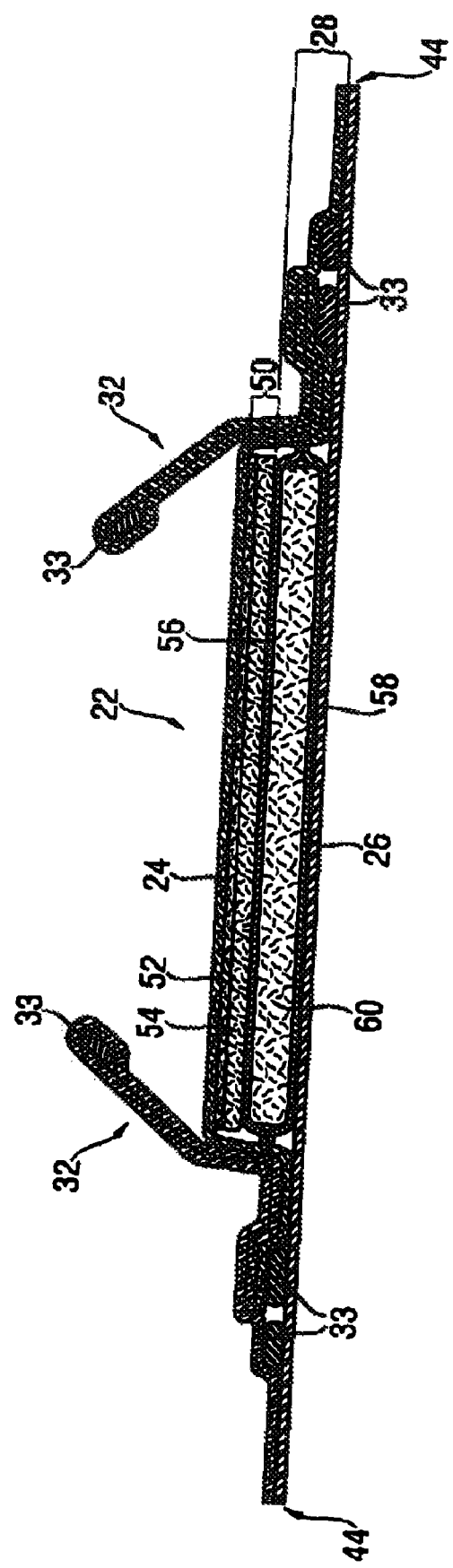

ABSORBENT ARTICLES COMPRISING HYDROPHILIC NONWOVEN FABRICS

CROSS REFERENCE TO RELATED APPLICATIONS

This application is a divisional application of U.S. application Ser. No. 10/674,670 filed Sep. 30, 2003, which is incorporated herein by reference.

FIELD OF THE INVENTION

Disclosed herein is a process for making hydrophilic fibers, which can be formed into a nonwoven fabric useful in disposable absorbent articles.

BACKGROUND OF THE INVENTION

Disposable absorbent articles such as diapers and adult incontinence products are well known in the art. Such disposable articles collect and retain urine and fecal material deposited thereon by the wearer.

Nonwoven fabrics made of synthetic fibers are commonly applied in absorbent articles, for example, as topsheet material or as core wrap to enclose the storage layer of the absorbent core. Such nonwoven fabrics are usually hydrophobic. However, for many applications in hygiene products it is necessary to have hydrophilic nonwoven. Therefore the nonwoven fabric has to be treated accordingly.

A common method for rendering nonwoven fabrics hydrophilic is coating the surface of the nonwoven with hydrophilic surfactants. As this coating does not lead to a tight, chemical bond between the nonwoven and the surfactant, the surfactant can be washed off during use when the absorbent article is wetted. The decrease in liquid strike through time is a desirable effect when the nonwoven is coated with surfactant. Liquid strike through refers to liquid passing through the nonwoven fabric with liquid strike through time referring to the time it takes for a certain amount of liquid to pass through the nonwoven. However, as the surfactant is washed off when coated nowoven fabrics are exposed to the liquid, the strike through time in the next gushes is increased again. This results in performance reduction during use for diapers comprising those nonwoven fabrics. Furthermore, at the same time as liquid strike through time decreases due to use of surfactants, surface tension of the liquid, which was in contact with the nonwoven fabric, is reduced. This reduction is undesirable, because it can cause increased urine leakage in a diaper. On the other side, any surfactants leading to reduced strike through time also reduces surface tension of the wash off.

Examples of typical surfactants are described in WO 93/04113 entitled "Method for hydrophilizing absorbent foam materials" and in WO 95/25495 entitled "Fluid acquisition and distribution member for absorbent core".

Another possibility to render a nonwoven fabric hydrophilic is by applying corona and plasma treatment.

Plasma is an ionized form of gas that can be obtained by ionizing a gas or liquid medium. Plasmas are widely used for the treatment of organic and inorganic materials to promote adhesion between various materials. Polymers that have chemically inert surfaces with low surface energies do not allow good coatings with bondings and adhesives. Thus, these surfaces are treated to make them receptive to bonding with other substrates, coatings, adhesives and printing inks. A method for producing plasma is described in U.S. Pat. No. 6,118,218 entitled "Steady-state glow-discharge plasma at atmospheric pressure".

Corona discharge is an electrical phenomenon, which occurs when air is exposed to a voltage potential high enough to cause ionization, thereby changing it from an electrical insulator to a conductor of electricity.

However, corona and plasma treatment lead to low coating durability upon storage of material, i.e. hydrophilicity decreases over time.

WO 00/16913 entitled "Durably wettable, liquid pervious webs" and WO 00/16914 entitled "Durably wettable, liquid pervious webs prepared using a remote plasma polymerization process" disclose webs with a hydrophilic coating applied by a plasma polymerization process. However, the drawback of this process is, that commercial application is constrained, because it is very slow and cannot be carried out continuously but needs a batch process.

Thus, there is a need for a hydrophilic coating of a nonwoven, which is durable upon storage, is not easily washed off when wetted and allows to achieve fast liquid strike through in multiple exposures to liquid without surface tension reduction of wash-off.

Methods of chemically grafting hydrophilic monomers are known in the art. For example U.S. Pat. No. 5,830,604 entitled "Polymeric sheet and electrochemical device using the same" issued to Raymond et al.; U.S. Pat. No. 5,922,417 entitled "Polymeric sheet" issued to Raymond et al.; and WO 98/58108 entitled "Non-woven fabric treatment" all refer to a process to produce nonwovens for use as seperator in electrochemical devices such as batteries.

EP 1 164 157 A1 entitled "Method of modifying polymeric material and use thereof" discloses a method of modifying polymeric material, which comprises the steps of an activation treatment and a hydrophilic polymer treatment in this order. The method optionally further comprises a solvent treatment, which is carried out prior to the activation treatment and/or further comprises monomer grafting carried out after the hydrophilic polymer treatment. The disadvantage of this method is, that it is very complex and comprises numerous steps. Moreover, treating a nonwoven with water-soluble polymers lead to a reduction in surface tension of water when such nonwoven is exposed to water.

It is one objective of the present invention, to provide absorbent articles, which comprise nonwoven fabrics with a durable hydrophilic coating.

It is a further objective of the present invention, to provide absorbent articles, comprising nonwoven fabrics with hydrophilic coatings, which are not washed off.

Moreover, it is an objective of the present invention to provide absorbent articles, which comprise nonwoven fabrics with low strike through times even after several gushes and which at the same time do not have a reduced surface tension when contacted with aqueous liquids.

It is a still further objective of the present invention to provide a process for making a nonwoven fabric, which are suitable for absorbent articles having the desired properties.

SUMMARY OF THE INVENTION

In order to provide a solution to the problems above, there is disclosed. A method for making a hydrophilic nonwoven from a plurality of treated fibers. The method comprises contacting a plurality of fibers with an aqueous solution that includes hydrophilic monomers, radical polymerization initiators, and agent molecules. The amount of radical polymerization initiator molecules is less than 2 wt % of the monomer molecules and at least three times the amount of the agent molecules by weight, based on the weight of the solution. The aqueous solution is contacted to the plurality of fibers, and the contacted fibers are exposed the to UV radiation such that hydrophilic polymers are chemically grafted to the surface of at least a part of the plurality of fibers by way of reactive radicals formed from at least one of (i) a reaction between a monomer molecule and a radical polymerization initiator molecule and (ii) a reaction between the fiber surface and a radical polymerization initiator molecule. The fibers are formed into a nonwoven, which has a liquid strike through time of less than 5 seconds for a fifth gush of liquid. The nonwoven provides a surface tension measurement of at least 65 mN/m according to the Determination of Surface Tension method.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 2 is a cross-sectional view of the disposable diaper shown in FIG. 1

DETAILED DESCRIPTION OF THE INVENTION

Definitions

Figure 1:
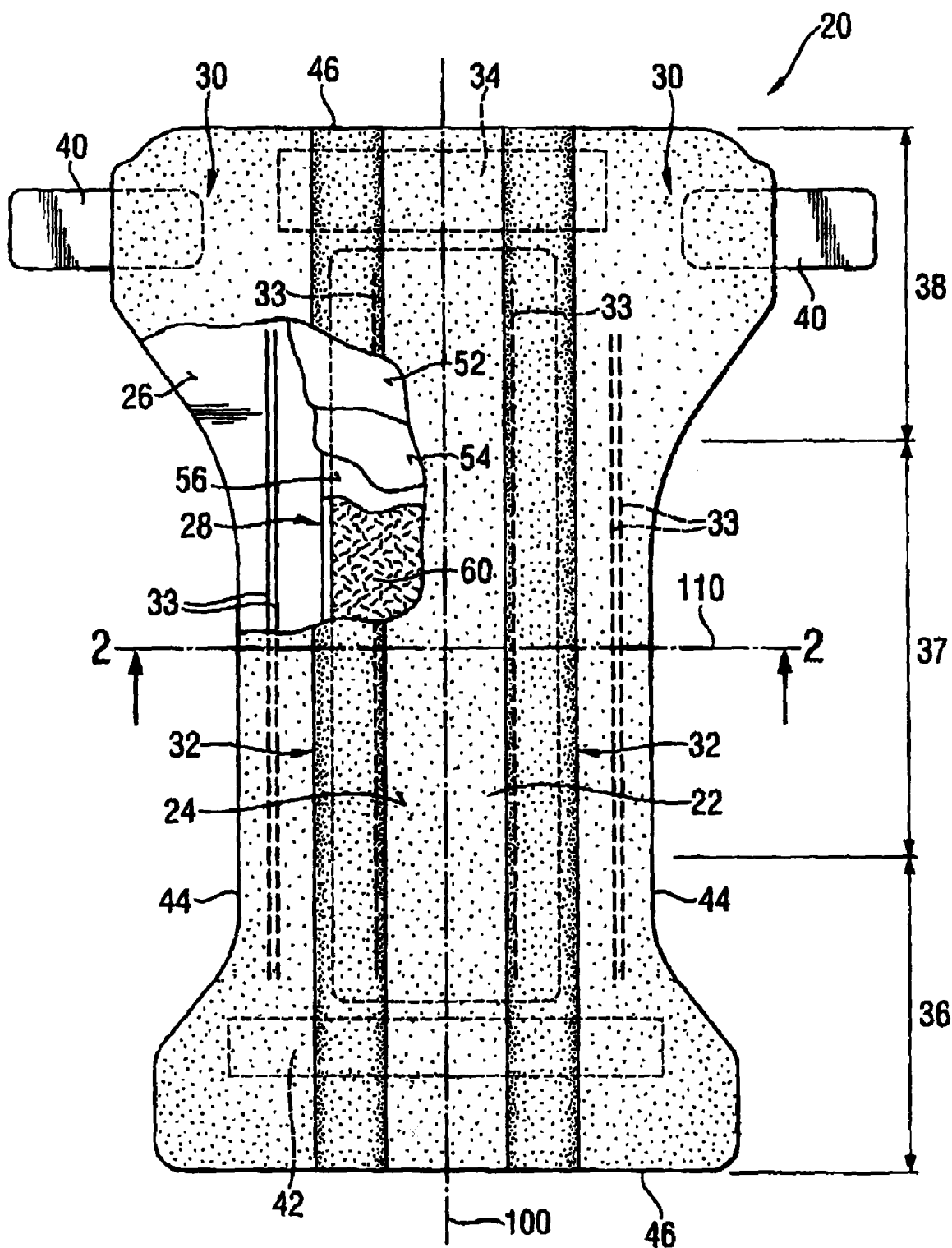
FIG. 1 is a top plan view of a disposable diaper, with the upper layers partially cut away.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, training pants, diaper holders and liners, sanitary napkins and the like.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The term "hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally coexisting. Conversely, a fiber or surface of the fiber is considered to be hydrophobic if the contact angle is greater than 90° and the fluid does not spread spontaneously across the surface of the fiber.

The terms "fiber" and "filament" are used interchangeably.

The terms "nonwoven fabric" and "nonwoven web" are used interchangeable.

The term "plurality of fibers" refers to fibers or filaments as well as to nonwoven fabrics.

Absorbent Articles

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 28 encased between the topsheet 24 and the backsheet 26. The chassis preferably further includes side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 preferably attached to the rear waist region 38 and a landing zone 42 attached to the front waist region 36. The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991;

and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 preferably attached to the rear waist region 38. In a preferred embodiment the fastening system further comprises a landing zone 42 attached to the front waist region 36. The fastening member is attached to the front waist region 36, preferably to the landing zone 42 to form leg openings and an article waist.

Diapers 20 according to the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

FIG. 2 shows a cross-sectionional view of FIG. 1 taken in the transverse axis 110. Starting from the wearer facing side the diaper comprises the topsheet 24, the components of the absorbent core 28, and the backsheet 26. The absorbent core preferably comprises an acquisition system 50, which comprises an upper acquisition layer 52 facing towards the wearer and a lower acquisition layer 54. In one preferred embodiment the upper acquisition layer comprises a non-woven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer 60.

The storage layer 60 is preferably wrapped by a core wrap material. In one preferred embodiment the core wrap material comprises a top layer 56 and a bottom layer 58. The top layer 56 and the bottom layer 58 can be provided from a non-woven material. One preferred material is a so-called SMS material, comprising a spunbonded, a melt-blown and a further spunbonded layers. The top layer 56 and the bottom layer 58 may be provided from two or more separate sheets of materials or they may be alternatively provided from a unitary sheet of material. Such a unitary sheet of material may be wrapped around the storage layer 60, e.g. in a C-fold.

The storage layer 60 typically comprises fibrous materials, mixed with superabsorbent, absorbent gelling materials. Other materials described above as suitable for the absorbent core 28 may also be comprised.

According to the present invention, preferably the topsheet 24 and/or the upper core wrap layer 56 and/or the lower core wrap layer 58 of the absorbent article are made of the hydrophilic nonwoven fabric described below in greater detail. Moreover, the hydrophilic nonwoven fabric according to the present invention is preferably used as acquisition material 52 and/or 54 in the absorbent core 28.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibres may be of natural or man-made origin. They may be staple or continuous filaments or be formed in situ.

Nonwoven fabrics can be formed by many processes such as meltblowing, spunbonding, carded. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. Example synthetic fibers, which are derived from natural fibers include but are not limited to rayon and lyocell, both of which are derived from cellulose, a natural polysaccharide fiber. Synthetic fibers, which are not derived from natural fibers can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are formed at about the same point in time, or by preformed fibers which can be laid into webs at a distinctly subsequent point in time. Example direct extrusion processes include but are not limited to: spunbonding, meltblowing, solvent spinning, electrospinning, and combinations thereof typically forming layers.

As used herein, the term "spunbonded fibers" refers to small diameter fibers, which are formed by extruding molten thermoplastic material as filaments from a plurality of fine, usually circular capillaries of a spinneret. Spunbond fibers are quenched and generally not tacky when they are deposited onto a collecting surface. Spunbond fibers are generally continuous.

As used herein, the term "meltblown fibers" means fibers formed by extruding a molten thermoplastic material through a plurality of fine, usually circular, die capillaries as molten threads or filaments into converging high velocity gas (e.g. air) streams, which attenuate the filaments of molten thermoplastic material to reduce their diameter. Thereafter, the meltblown fibers are carried by the high velocity gas stream and are deposited on a collecting surface to form a web of randomly disbursed meltblown fibers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof.

In a preferred embodiment of the present invention, the nonwoven fabric is made of polypropylene (PP) and/or polyethylene (PET). In another embodiment the nonwoven fabric is made of bicomponent fibers consisting of PP and PET.

For use as core wrap material the nonwoven fabric is preferably made by a combination of spunbond and meltblown process (SMMS) and the basis weights are preferably from 7 gsm to 30 gsm, more preferably from 8 gsm to 20 gsm, and even more preferably from 8 gsm to 15 gsm.

For use as topsheet material in the storage layer, the nonwoven fabric preferably comprises spunbond fibers. The basis weight of the topsheet is preferably from 10 to 30 gsm, more preferably from 15 gsm to 20 gsm. In another embodiment, the topsheet comprises a carded nonwoven fabric with preferred basis weights from 10 gsm to 25 gsm, more preferably from 15 gsm to 20 gsm.

For application as acquisition material in the absorbent core, the nonwoven is preferably made by a carding process and the basis weights are preferably from 20 to 200 gsm, more preferably from 40 to 100 gsm and even more preferably about 60 gsm. The material is further bonded, e.g. by resin-, or air-through thermal bonding processes.

Process for Making Permanently Hydrophilic Nonwoven Fabrics

The process of the present invention refers to the treatment of a plurality of fibers. If formed into nonwoven fabrics, the plurality of fibers is particularly suitable for absorbent articles. The process is very economic, because it comprises relatively inexpensive chemicals. Furthermore, the process is very fast. It can be run at line speeds of at least 200 m/min, more preferably at least 300 m/min and even more preferably at least 400 m/min.

The process for treating a plurality of fibers according to the present invention comprises the following steps:

Step a)

Providing a plurality of fibers. The fibers can be natural fibers (e.g. wool, silk, cellulose, cotton), man made fibers or synthetic fibers made of resins like polyamide, polypropylene, polyethylenes, polyester or polyamides. The fibers typically have diameters ranging from less than about 0.001 mm to more than about 0.2 mm.

Step b)

Providing an aqueous solution comprising hydrophilic monomers and radical polymerization initiators.

Preferably the ratio of monomer molecules to initiator molecules in the aqueous solution is at least 50 to 1. More preferably the ratio is at least 100 to 1, even more preferably the ratio is at least 500 to 1 and most preferably the ratio is at least 1000 to 1.

The aqueous solution comprises a hydrophilic monomer capable of radically polymerization. Preferably the monomer contains at least one unsaturated double bond according to the general formula $R_1R_2C=CR_3R_4$, with $R_1$ and $R_2$ preferably being hydrogen atoms. More preferably the hydrophilic monomer comprises a group, which can react with an acid or base to form a salt. Examples of suitable monomers are acrylic acid and its derivates (e.g. methacrylic acid, ethylacrylic acid), styrene sulphonic acid and its derivates, vinyl acetate, maleic anhydride and vinyl pyridine. In a preferred embodiment of the invention acrylic acid or its salt is used as monomer.

The aqueous solution further comprises a radical polymerization initiator. Preferably the initiator is capable of forming reactive radicals upon activation with light. Examples for suitable radical polymerization initiators are benzophenone and its derivates, benzoyl peroxide or azobisisobutyronitrile (AIBN).

Preferably the aqueous solution further comprises an agent, which reduces homopolymerization of the hydrophilic monomers in the solvent. Examples for such agents are iron-II-salts, copper-II-salts (e.g. iron-II-sulphate) or mixtures thereof. At least 3 times more initiator molecules than agent molecules should be present in the aqueous solution, more preferably at least 5 times more.

Optionally the aqueous solution further comprises a surfactant and/or an organic solvent to improve wetting of the plurality of fibers by the aqueous solution. However, only those surfactants should be applied, which do not interfere with the polymerization. Examples for suitable organic solvents are various alcohols with alkyl chains of different lengths and different degrees of branching.

Step c)

Contacting the plurality of fibers with an aqueous solution comprising hydrophilic monomers and radical polymerization initiator. The hydrophilic monomers are capable to undergo a radical polymerization process. The aqueous solution may further comprise an agent, which reduces homopolymerization of the hydrophilic monomers. Moreover, the aqueous solution may further comprise surfactants and/or organic solvents.

To achieve a homogenous application of the aqueous solution on the plurality of fibers, kiss-roll coating or spraying are particularly suitable. Both methods are well known in the art.

In kiss-roll coating, the aqueous solution is kept in a suitable bath. A rotating cylinder or any other device suitable for this process, is contacting the solution with at least a part of its surface. Thus, the aqueous solution is spread on the surface of the cylinder. The plurality of fibers is brought into contact with the cylinder while the cylinder already has the aqueous solution spread on its surface. In this process, the amount of aqueous solution applied on the plurality of fiber can be controlled easily and it is possible to avoid soaking the plurality of fiber with aqueous solution.

Hence, the add-on level of polymer grafted to the fiber surface can be controlled, which is difficult in a process, where the plurality of fibers is contacted directly with a bath of aqueous solution. Moreover, the amount of aqueous solution necessary for the process can be reduced to a minimum.

Alternatively to the kiss-roll coating, the aqueous solution can also be sprayed on the surface of the plurality of fibers. Like the kiss-roll coating, spraying enables low and easily controllable add-on level of aqueous solution, which is preferred in the present invention.

A preferred solvent according to the present invention is transparent to UV radiation, has no atoms abstactable when exposed to radiation and does not adversely affect the properties of the fibers. An example for a suitable solvent is water.

Step d)

Exposing the plurality of fibers to UV radiation after contacting the plurality of fibers with the aqueous solution.

In a preferred embodiment of the present invention, a standard medium mercury lamp emitting UV-A (315-400 nm and/or UV-C (200-280 nm) radiation is used. Suitable lamps are for example available from IST Metz GmbH, Neurtingen, Germany. Preferred lamps are characterized by an energy input from 160 W/cm to 200 W/cm of length of the lamp.

The energy level required to perform the reaction depends on the particular monomer chemistry, the required add-on level, the thickness of the fiber, the line speed and the distance between nonwoven fiber and energy source.

In a preferred embodiment the plurality of fibers is positioned in the smallest possible distance from the UV radiation source without melting, burning or otherwise damaging the fibers.

Due to the high dosage of UV radiation and the relatively low amount of aqueous solution applied on the surface of the plurality of fibers, it is sufficient to expose the plurality of fibers to UV radiation for up to 2 seconds, more preferably for up to 1 second and even more preferably up to 0.5 second.

The step of exposing the plurality of fibers to UV radiation is preferably carried out under inert gas atmosphere, e.g. nitrogen, to reduce access of oxygen to the reaction medium.

The radical polymerization initiator preferably is capable of forming reactive radicals upon activation with light. The radicals formed will then react with monomers and/or plurality of fibers to generate polymers chemically attached to the surface of the plurality of fibers. Some polymers will also be in the aqueous solution with no bonding to the plurality of fibers. The polymer chains bonded to the plurality of fibers may be linear or branched, but preferably are not cross-linked to each other.

As the process includes the use of a radical polymerization initiator in the aqueous solution, at least a fragment of these radical polymerization initiator molecules will be present in at least a part of the polymer chains chemically grafted to the fiber surface in the course of the polymerization process. The initiator molecules are fragmented by homolytic splitting of a covalent bond within the molecules to create radicals, which are able to start the polymerization. Fragmentation of the initiator molecules is initiated by UV radiation. The polymerisation results in a plurality of fibers with the hydrophilic monomers and at least fragments of the radical polymerization initiator molecules of the aqueous solution copolymerized to the surface of the fibers. However, as in the aqueous solution the amount of hydrophilic monomers is much higher than the amount of radical polymerization initiator molecules, only a small amount of radical polymerization initiator molecules will be part of the polymer chain chemically grafted to the fiber surface.

It is understood, that the hydrophilic polymer does not have to cover the total surface of the fibers.

Some polymers, which are not chemically grafted to the fiber surface and/or unreacted hydrophilic monomers and/or radical polymerization initiator molecules might still be present on the surface of the plurality of fibers without being chemically bonded. Therefore, washing of the plurality of fibers is optionally carried out after UV radiation to remove those molecules, which are not chemically grafted to the fiber surface. If the plurality of fibers provided for the process is not a nonwoven fabric but individual fibers or filaments, these individual fibers or filaments might be formed into a nonwoven fabric. In this case the washing step can be carried out before or after the plurality of fibers was formed into a nonwoven fabric.

To receive hydrophilic fibers, which are particularly suitable in an absorbent article, a add-on level of 0.3 wt % to 10 wt % on the plurality of fibers is preferred. More preferred are add-on levels of 0.3 wt % to 5.0 wt % and even more preferred the add-on levels are 0.3 wt % to 1.5 wt %. As used herein, the term "add-on level" refers to the weight of the polymer chemically grafted to the surface of the fiber in respect of the weight of fibers.

In one embodiment of the invention, the plurality of fibers provided for the process is not a nonwoven fabric but individual fibers or filaments. In this embodiment the individual fibers or filaments might be formed into a nonwoven fabric in an further process step at any point of the process, for example before contacting the plurality of fibers with the aqueous solution or after exposing the plurality of fibers to UV radiation. In case the below mentioned optional washing step is also carried out, making a nonwoven fabric from the fiber can take place before or after this washing step. The additional process step of forming the individual fibers or filaments into a nonwoven fabric may comprise at least a first plurality of fibers and a second plurality of fibers, wherein the first plurality of fibers is different from said second plurality of fibers. This difference might for example be due to different hydrophilic monomers or different radical polymerization initiators in the aqueous solution. The difference might further be due a different exposure of the plurality of fibers to UV radiation (e.g. different exposure time). In one embodiment of the invention, only the first plurality of fibers is treated to have polymers comprising hydrophilic monomer molecules and at least parts of the radical polymerization initiator molecules chemically grafted to the surface of the fibers. In this embodiment the nonwoven fabric formed from the different pluralities of fibers comprises treated and untreated fibers.

In another embodiment of the invention, the plurality of fibers provided for the process is a nonwoven fabric.

Absorbent articles according to the present invention comprise nonwoven fabrics with hydrophilic monomers and at least fragments of radical polymerization initiator molecules copolymerized to the surface of the fibers of the nonwoven fabrics. In the polymer the amount of radical polymerization initiator molecules is up to 2 wt % of the monomer molecules, more preferably up to 1 wt %.

The hydrophilic monomer molecules chemically grafted to the surface of at least a part of the plurality of fibers, which are comprised by the absorbent article of claim 1, preferably contain at least one unsaturated double bond according to the general formula $R_1R_2C=CR_3R_4$, with $R_1$ and $R_2$ preferably being hydrogen atoms. More preferably the monomers comprise a group, which can react with an acid or base to form a salt. In a preferred embodiment of the invention, the hydrophilic monomer is acrylic acid or its salt. Examples of suitable polymers are acrylic acid and its derivates (e.g. methacrylic acid, ethylacrylic acid), styrene sulphonic acid and its derivates, vinyl acetate, maleic anhydride and vinyl pyridine. In a preferred embodiment of the invention acrylic acid or one of its salt is used as monomer.

According to the invention, the nonwoven fabric may comprise only fibers with hydrophilic monomers and radical polymerization initiator molecules copolymerized to the surface of the fibers (treated fibers).

In another embodiment, the nonwoven fabric comprises at least a first plurality of fibers and a second plurality of fibers, both of which have been treated according to the process described above. The first plurality of fibers is different from the second plurality of fibers. This difference might for example be due to different add-on levels, different hydrophilic monomers or different radical polymerization initiator.

In still another embodiment of the present invention, the nonwoven fabric may comprise a blend of treated fibers and untreated fibers with no polymers chemically bonded to their surface. Preferably, the amount of treated fibers is at least 10% of the total amount of fibers in the non-woven fabric. More preferably the amount of treated fibers is at least 25%, even more preferably the amount of treated fibers is at least 50% and most preferably the amount of treated fibers is at least 70% of the total amount of fibers.

Due to this hydrophilic coating, the nonwoven fabric has fast liquid strike through in multiple gushes. As the coating is chemically attached to the fibers, no meaningful part of it is washed off when the nonwoven fabric is exposed to aqueous solvents. Therefore, no significant surface tension reduction occurs when nonwoven fabric is exposed to aqueous solutions. Strike through and surface tension are determined with the tests described below in detail. The surface tension of aqueous wash-off from the treated nonwoven fabric is at least 65 mN/m, more preferably at least 68 mN/m and even more preferably at least 71 mN/m. The liquid strike through time of the treated nonwoven fabric is less than 5 seconds for a fifth gush of liquid with every gush comprising 5 ml of saline solution. More preferably, liquid strike through time is less than 4.5 seconds for a fifth gush, even more preferably is less than 4.0 seconds for a fifth gush and most preferably is less than 3.5 seconds for a fifth gush of liquid. Hence, liquid strike through is maintained even after several gushes, because the hydrophilic coating is not considerably washed off during use.

The absorbent articles comprising nonwoven fabrics according to the present invention have high durability upon storage. After storage for at least 10 weeks, more preferably after storage for at least 20 weeks, strike through times after one or more gushes will not decrease by more than 10%, and more preferably by more than 5%.

All patent documents cited herein and assigned to The Procter & Gamble Company are incorporated herein by reference.

Test Methods

Determination of Surface Tension

The surface tension (unit: mN/m) is determined according to the following test.

Apparatus:

Equipment: K10 tensiometer provided by Krüss GmbH, Germany or equivalent. The vessel elevation speed should be 4 mm/min. Liquid surface height should be sensed automatically when using a plate or a ring. The equipment must be able to adjust the sample position automatically to the correct height. Precision of test should be +/−0.1 mN/m.

Procedure:

1. Pouring 40 ml of saline (0.9 wt % NaCl in deionized water) into a cleaned beaker.

2. Testing the surface tension with a platinum ring or a platinum plate. The surface tension should be 71-72 mN/m at 20° C.

3. Cleaning the beaker with deionized water and isopropanol and burning it out with a gas burner for a few seconds. Waiting until equilibrate to room temperature is reached.

4. Placing 10 60×60 mm pieces of test nonwoven into a cleaned beaker. The nonwoven should have a basis weight of at least 10 gsm.

5. Adding 40 ml of saline (0.9 wt % NaCl in deionized water).

6. Stirring with a clean surfactant-free plastic stick for 10 seconds.

7. Letting the solution with nonwoven stand for 5 minutes.

8. Stirring again for 10 seconds.

9. Removing the nonwoven from the solvent with a clean surfactant-free plastic stick.

10. Letting the solution stand for 10 minutes.

11. Testing surface tension with a platinum plate or platinum ring.

Determination of Strike Through

The test is carried out based on Edana Method 150.3-96 (February 1996) Liquid Strike Through Time. As a major modification compared to the Edana Method, the test described below does not only measure the first gush but several subsequent gushes.

Apparatus
  Lister Strike Through Equipment:
    Funnel fitted with magnetic valve: Rate of discharge of 25 ml in 3.5 (±0.25) seconds
    Strike through plate: Constructed of 25 mm thick acrylic glass. The total weight of the plate must be 500 g. The electrodes should be of non-corrosive material. The electrodes are set in (4.0 mm×7.0 mm) cross section grooves, cut in the base of the plate and fixed with quick setting epoxy resin.
    Base plate: A square of acrylic glass 125 mm×125 mm approximately.
  Ring stand to support the funnel
  Electronic Timer measuring to 0.01 seconds
  Burette with 50 ml capacity
  Core filter paper Ahlström Grade 989 or equivalent (average Strike Through time 1.7 s+−0.3 s, dimensions: 10×10 cm)

Procedure

1. Carefully cutting the required number of samples, 12.5 cm×12.5 cm with touching the sample only at the edge of the sample.

2. Taking 10 plies of core filter paper.

3. Placing one sample on the set of 10 plies of filter paper on the base plate. The sample should be positioned on the filter paper in such a way that the side of the nonwoven, which is intended to face the user's skin (when applied in an absorbent article) is uppermost.

4. Placing the strike through plate on top with the center of the plate over the center of the test piece.

5. Centering the burette and the funnel over the plate.

6. Ensuring that the electrodes are connected to the timer. Switching on the timer and set the clock to zero.

7. Filling the burette with saline solution (0.9 wt % NaCl in deionized water).

8. Keeping the discharge valve of the funnel closed and run 5.0 ml of liquid (=One gush) from the burette into the funnel.

8. Opening the magnetic valve of the funnel to discharge 5.0 ml of liquid. The initial flow of liquid will complete the electrical circuit and start the timer. It will stop when the liquid has penetrated into the pad and fallen below the level of the electrodes in the strike through plate.

9. Recording the time indicated on the electronic timer.

10. Waiting for 60 seconds and going back to point 6 for the second, the third gush and any subsequent gush, with each gush comprising 5 ml of liquid.

11. Report: Time for the $1^{st}$, $2^{nd}$ and any subsequent gush in seconds.

What is claimed is:

1. A method for making a hydrophilic nonwoven from a plurality of treated fibers, comprising:
   providing a plurality of fibers;
   providing an aqueous solution comprising hydrophilic monomers, radical polymerization initiators, and agent molecules, wherein the amount of radical polymerization initiator molecules is less than 2 wt % of the monomer molecules and at least three times the amount of the agent molecules by weight based on the weight of the solution;
   contacting the plurality of fibers with the aqueous solution;
   exposing the plurality of fibers to UV radiation such that hydrophilic polymers are chemically grafted to the surface of at least a part of the plurality of fibers by way of reactive radicals formed from at least one of (i) a reaction between a monomer molecule and a radical polymerization initiator molecule and (ii) a reaction between the fiber surface and a radical polymerization initiator molecule;
   forming the fibers into a nonwoven, wherein the nonwoven has a liquid strike through time of less than 5 seconds for a fifth gush of liquid and wherein the nonwoven provides a surface tension measurement of at least 65 mN/m according to the Determination of Surface Tension method; and
   incorporating the nonwoven into a disposable absorbent article wherein the add-on level of the hydrophilic polymer is from 0.3 wt % to 10 wt % based on the weight of the fibers.

2. The method of claim 1, wherein said method includes providing a second plurality of fibers, the second plurality of fibers being chemically different from the first plurality of fibers.

3. The method of claim 2, wherein the second plurality of fibers have not been treated.

4. The method of claim 1, wherein the agent molecules are added to reduce homopolymerisation of the monomers.

5. The method of claim 1, further comprising washing the plurality of fibers after the fibers are exposed to UV radiation.

6. The method of claim 1, wherein said strike through time after the first and the fifth gush of the nonwoven fabric does not decrease more than 5% after storage of the nonwoven for at least 10 weeks.

7. The method of claim 1, wherein said monomer molecule comprises at least one unsaturated double bond.

8. The method of claim 1, wherein said monomer molecule comprises a group that is able to react with an acid or base to form a salt.

9. The method of claim 8, wherein said monomer molecule comprises acrylic acid or its salt.

* * * * *